(12) United States Patent
An et al.

(10) Patent No.: US 7,424,094 B2
(45) Date of Patent: Sep. 9, 2008

(54) GAMMA RADIATION IMAGING SYSTEM FOR NON-DESTRUCTIVE INSPECTION OF THE LUGGAGE

(75) Inventors: Jigang An, Beijing (CN); Yisi Liu, Beijing (CN); Xincheng Xiang, Beijing (CN); Haifeng Wu, Beijing (CN); Zhifang Wu, Beijing (CN); Liqiang Wang, Beijing (CN)

(73) Assignee: Tsinghua University, Beijing (CN)

( * ) Notice: Subject to any disclaimer, the term of this patent is extended or adjusted under 35 U.S.C. 154(b) by 355 days.

(21) Appl. No.: 10/542,740

(22) PCT Filed: Jun. 25, 2004

(86) PCT No.: PCT/CN2004/000693

§ 371 (c)(1),
(2), (4) Date: Jul. 19, 2005

(87) PCT Pub. No.: WO2005/001457

PCT Pub. Date: Jan. 6, 2005

(65) Prior Publication Data

US 2006/0182218 A1    Aug. 17, 2006

(30) Foreign Application Priority Data

Jun. 27, 2003  (CN) .................................. 03 1 47875
Mar. 5, 2004  (CN) .................... 2004 2 0005845 U

(51) Int. Cl.
*G01N 23/04*  (2006.01)

(52) U.S. Cl. ........................................... 378/57; 378/62
(58) Field of Classification Search ...................... 378/4, 378/19, 57, 63, 70, 145, 147, 154, 160, 901
See application file for complete search history.

(56) References Cited

U.S. PATENT DOCUMENTS 5,182,764 A    1/1993   Peschmann et al. ........... 378/57

(Continued)

FOREIGN PATENT DOCUMENTS

| CN | 1242519 A | 1/2000 |
| CN | 1358316 A | 7/2002 |
| CN | 1401996 A | 3/2003 |
| CN | 1401997 A | 3/2003 |

*Primary Examiner*—Irakli Kiknadze
(74) *Attorney, Agent, or Firm*—Occhiuti Rohlicek & Tsao LLP

(57) ABSTRACT

Gamma radiation imaging system for non-destructive inspection of the luggage contains a DR sub-system, which obtains the projected image of the luggage by translationally scanning, and a CT sub-system, which obtains the tornograph image of the luggage by rotating scanning. Said DR sub-system includes a fixed gantry, a conveyor system, a radiation source mounted on the fixed gantry, front and back collimators, and the array detector. Said CT sub-system includes a rotating gantry, a conveyor system, a radiation source mounted on the rotating gantry, front and back collimators, and the array detector, wherein, the radiation source in said CT sub-system is $^{192}$Ir or $^{75}$Se radioactive isotope gamma source with high specific activity. Said gamma source is enclosed in a shield chamber with a projecting opening. The shield chamber is mounted on said rotating gantry. Said array detector is adapted for detecting gamma ray of $^{192}$Ir or $^{75}$Se radioactive isotope; The radiation source in said DR sub-system is $^{192}$Ir or $^{75}$Se radioactive isotope gamma source with high specific activity, said gamma source is enclosed in a shield chamber with a projecting opening. The shield chamber is mounted on said fixed gantry. Said array detector is adapted for detecting gamma ray of $^{192}$Ir or $^{75}$Se radioactive isotope.

9 Claims, 5 Drawing Sheets

U.S. PATENT DOCUMENTS

| | | | |
|---|---|---|---|
| 5,260,982 A | 11/1993 | Fujii et al. | 378/87 |
| 5,838,759 A * | 11/1998 | Armistead | 378/57 |
| 6,875,377 B1 * | 4/2005 | Shilton | 252/644 |
| 7,045,787 B1 * | 5/2006 | Verbinski et al. | 250/358.1 |
| 7,082,186 B2 * | 7/2006 | Zhao et al. | 378/57 |
| 2002/0097835 A1 * | 7/2002 | Fenkart et al. | 378/57 |

* cited by examiner

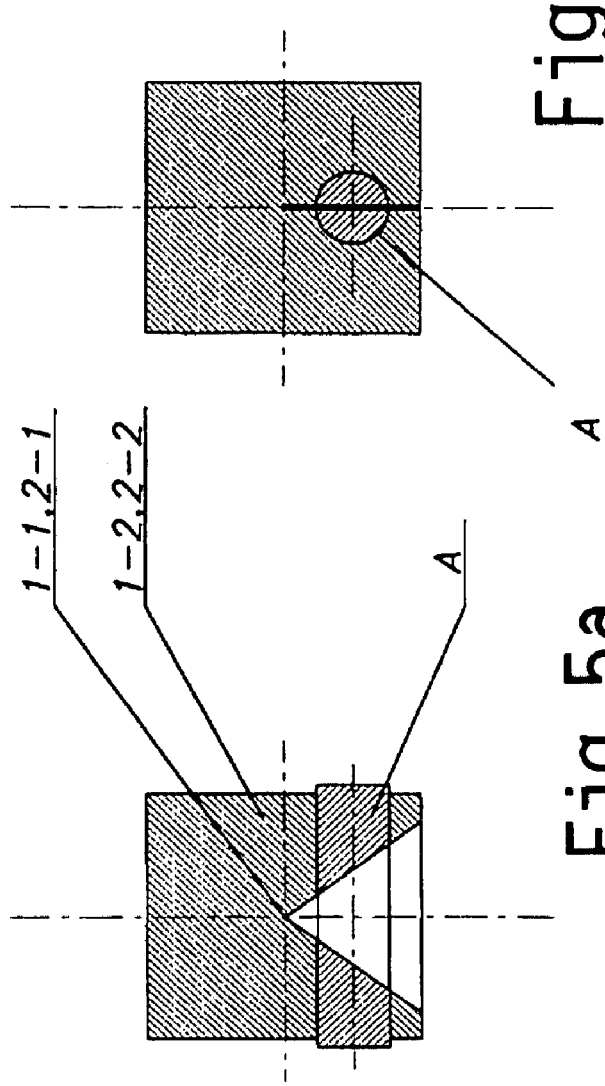
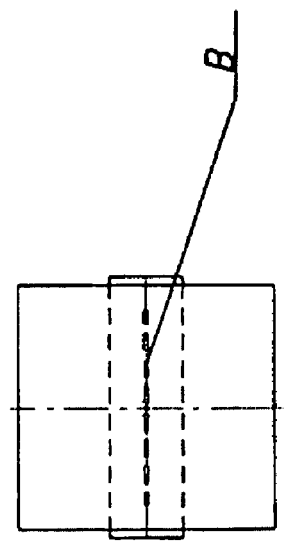
Fig.5a  Fig.5b  Fig.5c

GAMMA RADIATION IMAGING SYSTEM FOR NON-DESTRUCTIVE INSPECTION OF THE LUGGAGE

FIELD OF THE INVENTION

A γ radiation imaging nondestructive inspection system pertains to the field of nuclear technology application, in particular, it relates to the field of radiation imaging inspection for cases or luggage.

BACKGROUND OF THE INVENTION

All of the existing radiation imaging inspection systems for cases or luggage employ an X ray machine as a radiation source, high voltage of which is from 100 to 200 kV. Currently, the widely used X ray inspection systems for cases obtain a projection picture of a case through line scanning. In the projection picture, the images of the articles inside the case overlap on each other, while the grayscale of pixels of the images depends on the total mass thickness along the projection path. It is difficult to distinguish the material property of the articles from the projection picture of the case provided by such a DR type radiation imaging inspection system, thus it is insufficient to satisfy the requirement for searching the explosive, drug and flammable dangerous articles. In order to overcome this drawback, some major airports in USA begin to install a new radiation imaging case inspection device (disclosed by U.S. Pat. No. 5,182,764 and U.S. Pat. No. 5,367,552). Actually, the inspection device is in the form of tandem combination of the above-mentioned DR type X ray inspection system with the CT type X ray inspection system, which distinguishes the material property of the articles through the density based on the tomographic image achieved by the X-ray CT system. In order to increase the pass-through rate, the projection picture of the case is first obtained from the X ray DR inspection system, then it is determined which portions of the case require a further CT inspection based on the projection picture, finally the X-ray CT inspection system is adopted to obtain the tomographic images for these portions so as to search the illicit or dangerous articles such as explosive, drug and flammable articles; at the same time, if searched, mark them and generate an alarm.

Such a novel case inspection system still uses X ray machine as a radiation source, in which, the X ray machine of the CT inspection system has to rotate rapidly around the case. The major defects of this kind of X ray machine inspection system are:

1. The mean energy of X ray is low.

The high voltage of the above-mentioned X ray machine inspection system is from 100 to 200 kV, so the mean energy of resulted X-ray is limited to 30-70 keV. Such a low X ray energy leads to a poor penetration ability of the inspection system, thus no satisfactory inspection effect for relatively heavy cases can be achieved.

2. The configuration of the X ray machine is too complex and ponderous.

For the part of the CT inspection system, the main elements of the X ray machine, including a X-tube device and a high-voltage power supply, have to rotate around the object at a high speed (e.g. 720°/s) together with an array detector so as to increase the pass-through rate. However, the ponderous and complex X-tube device and high-voltage supply make it difficult to realize high rotary speed.

3. The lifetime is short

Since the operational lifetime of X-tube of CT inspection device is determined by the total complete tomographic scanning times, the higher the throughput rate (the number of inspected cases per unit time) is, the shorter the continuous working period of the X-tube is. For example, the X-tube of a CT inspection device can generally accomplish 100 thousand times of tomographic scan. Assumed that the pass-through rate is 360 cases per hour, and 3 times of tomographic scan process for each case, then the operational lifetime of X-tube will be only about 92 hours. In terms of 8 working hours per day, then the X-tube needs to be updated every 12 days, which greatly increases the operation cost and maintenance workload for such a X ray inspection system.

4. The irradiation field of the X-ray radiation is small

Limited by its generating mechanism, the space distribution of the X-ray is uneven, which has a preshoot character. Generally, the expanding angle of irradiation field of 100-200 kV X ray machine is about 42°. Therefore, in order to accommodate the X-ray irradiation field with the inspected object, the size of CT device must be large enough, which leads to the increase in both occupied land and weight of the equipment.

5. The cost is expensive

The price of the compact type high-voltage supply and X-ray tube device capable of moving rapidly together with the rotary frame is very expensive. If taking other elements into consideration, the total price of the case inspection device including the CT inspection system is nearly as high as 1 million dollars in US. This will inevitably restrict the wide application of this kind of inspecting device.

SUMMARY OF THE INVENTION

An object of the present invention is to resolve the technical problem of the current X ray inspection system, to provide a radiation imaging system for nondestructive inspection of a case, by using the γ-ray activity of radioactive isotope element ($^{192}$Ir or $^{75}$Se) with intermediate or low energy as radiation sources. The inspection system according to present invention possesses higher radiation energy, has stronger penetration ability, can obtain a high quality image and is capable of distinguishing the material properties. In addition, it has a low cost, small size and long operational lifetime, and its CT subsystem can perform high-speed rotation scanning, which helps to realize a high pass-through rate for detecting cases and luggage.

The present invention provides A γ radiation imaging system for nondestructive inspection of cases or luggage, comprises a DR subsystem for obtaining a projected luggage picture by line scanning, and a CT subsystem for obtaining a tomographic luggage image by rotary scanning, the DR subsystem includes a stationary frame, a conveying mechanism, and, a radiation source, a front collimator and a rear collimator, and an array detector, which are fixed onto the stationary frame; the CT subsystem includes a rotary frame, a conveying mechanism, and, a radiation source, a front collimator and a rear collimator, and an array detector, which are fixed onto the rotary frame, characterized in that, The radiation source of the CT subsystem is $^{192}$Ir or $^{75}$Se radioactive isotope γ-ray source with a high specific activity, which is enclosed in a shielding chamber with a projecting opening, the shielding chamber being fixed onto the rotary frame, the array detector is suitable for detecting γ rays of $^{192}$Ir or $^{75}$Se radioactive isotope, The radiation source of DR subsystem is $^{192}$Ir or $^{75}$Se radioactive isotope γ-ray source with a high specific activity, which is enclosed in a shielding chamber with a projecting opening, the shielding chamber being fixed onto the stationary frame, the array detector is suitable for detecting γ rays of $^{192}$Ir or $^{75}$Se radioactive isotope.

It is further characterized in that the activity of $^{192}$Ir or $^{75}$Se radioactive isotope γ-ray source in both the CT subsystem and the DR subsystem is lower than 11 TBq. The array detector in the CT subsystem is one of a gas-pressurized array ion-chamber, a multi-wire proportional chamber, a Geiger tube array, a scintillation detector or a semiconductor array detector. The array detector in the DR subsystem is one of a scintillator-photodiode array detector or a gas-pressurized array ion-chamber. The expanding angle of irradiation field of the γ-ray source shielding chambers in both the CT subsystem and the DR subsystem is greater than 40°.

The present invention provides another γ radiation imaging system for nondestructive inspection of cases or luggage, comprises a DR subsystem for obtaining a projection picture of luggage by line scanning, and a CT subsystem for obtaining a tomographic luggage image by rotary scanning, the DR subsystem includes a stationary frame, a conveying mechanism, and, a radiation source, a front collimator and a rear collimator, and an array detector, which are fixed onto the stationary frame; the CT subsystem includes a rotary frame, a conveying mechanism, and, a radiation source, a front collimator and a rear collimator, and an array detector, which are fixed onto the rotary frame, wherein, The radiation source of the CT subsystem is $^{192}$Ir or $^{75}$Se radioactive isotope γ-ray source with a high specific activity. The γ-ray source is enclosed in a shielding chamber with a projecting opening, the shielding chamber being fixed onto the rotary frame, the array detector is suitable for detecting γ rays of $^{192}$Ir or $^{75}$Se radioactive isotope; the radiation source of the DR subsystem is X-ray machine.

It is further characterized by that the activity of $^{192}$Ir or $^{75}$Se radioactive isotope γ-ray source in the CT subsystem is lower than 11 TBq.

The array detector in the CT subsystem is one of a gas-pressurized array ion-chamber, a multi-wire proportional chamber, a Geiger tube array and scintillation detector or a semiconductor array detector. The expanding angle of irradiation field of the γ-ray source shielding chambers □in the CT subsystem is greater than 40°.

Test result has shown that the γ radiation imaging system for nondestructive inspection of cases or luggage according to the present invention provides higher radiant energy, stronger penetrating capability, low cost, long operational lifespan and small volume. It is especially advantageous for improving rotary scanning speed for the CT subsystem, as well as realizing a high pass-through rate.

BRIEF DESCRIPTION OF THE DRAWINGS

FIG. 5a is a front view of the radiation source-shielding chamber with a shielding valve;

FIG. 5b is a side view of FIG. 5a;

FIG. 5c is a top view of FIG. 5a.

DESCRIPTION OF THE PREFERRED EMBODIMENT

The detailed embodiment of the present invention will be described with reference to the figures.

Figure 1:
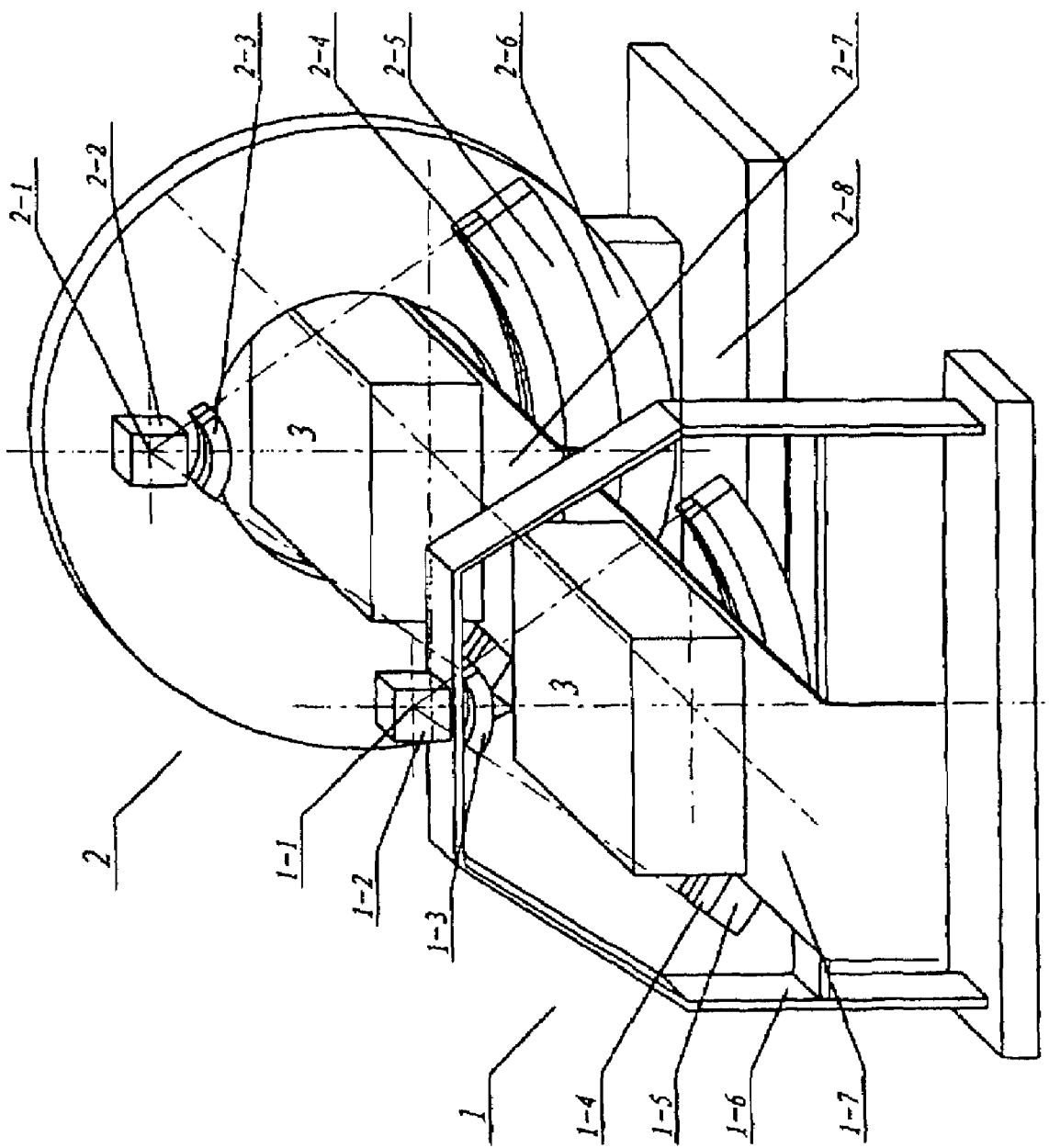
FIG. 1 is a general structure view of the radiation imaging system for nondestructive inspection of cases or luggage.
Figure 2:
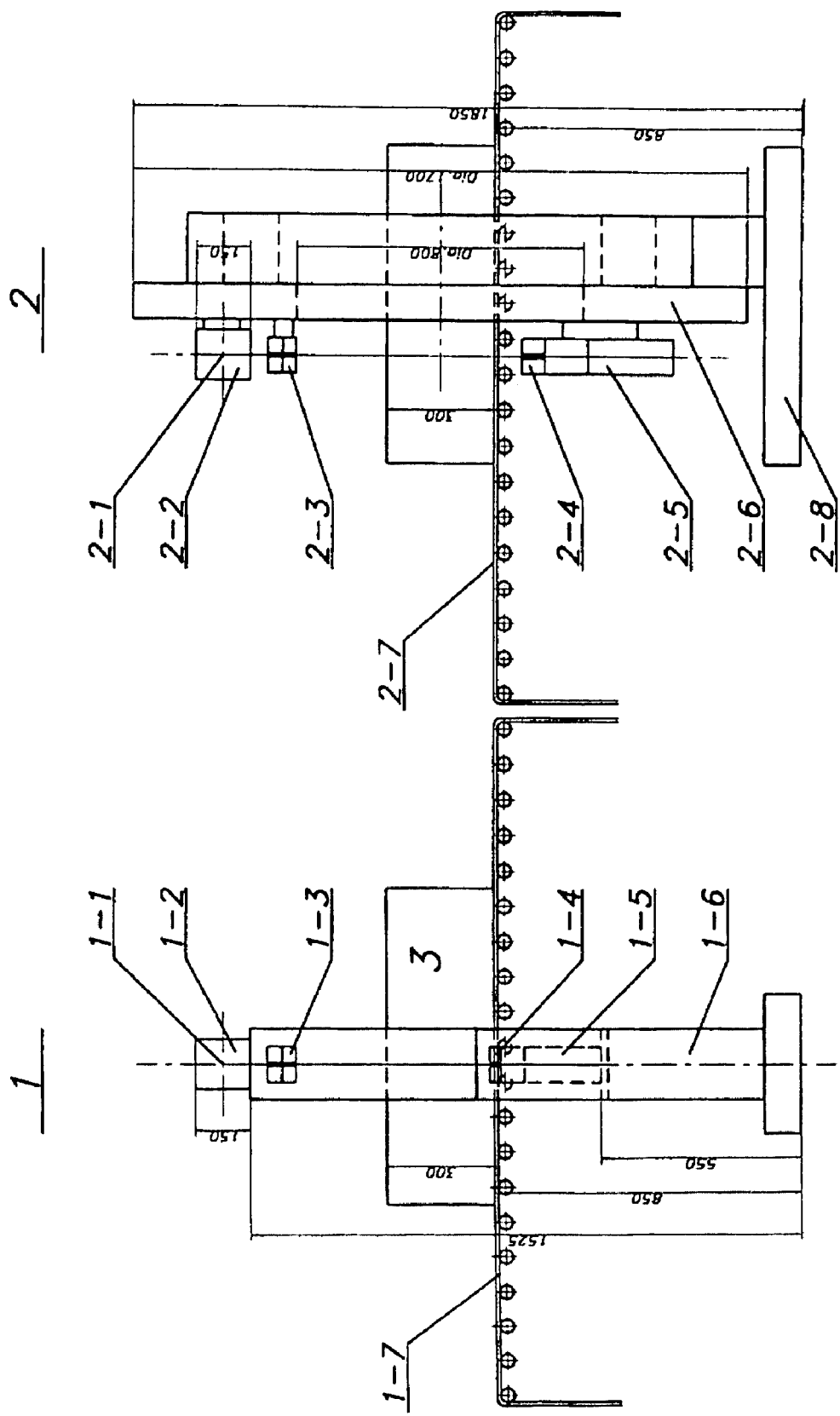
FIG. 2 is a side view of the radiation imaging system for nondestructive inspection of cases or luggage.
Figure 3:
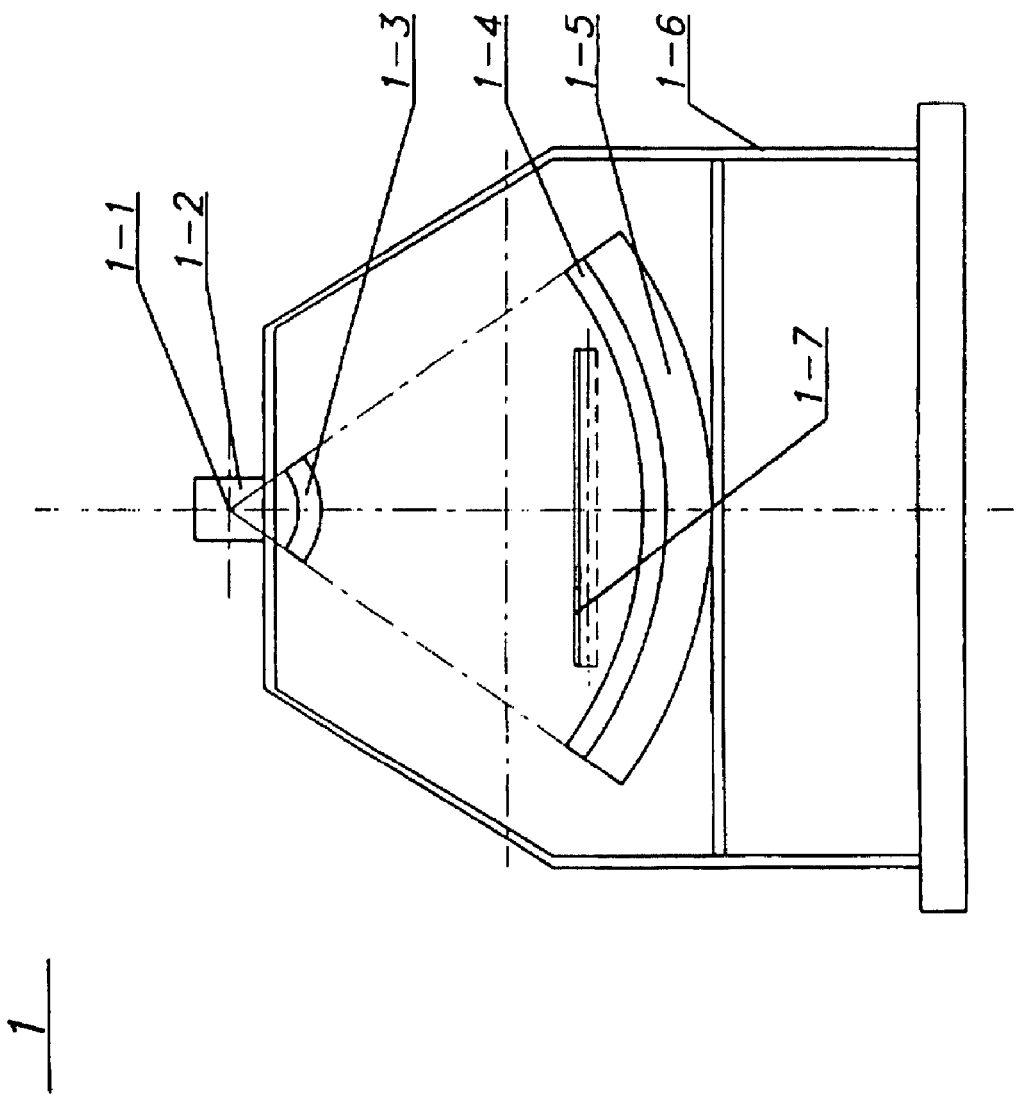
FIG. 3 is a front view of a DR subsystem of the radiation imaging system for nondestructive inspection of cases or luggage.
Figure 4:
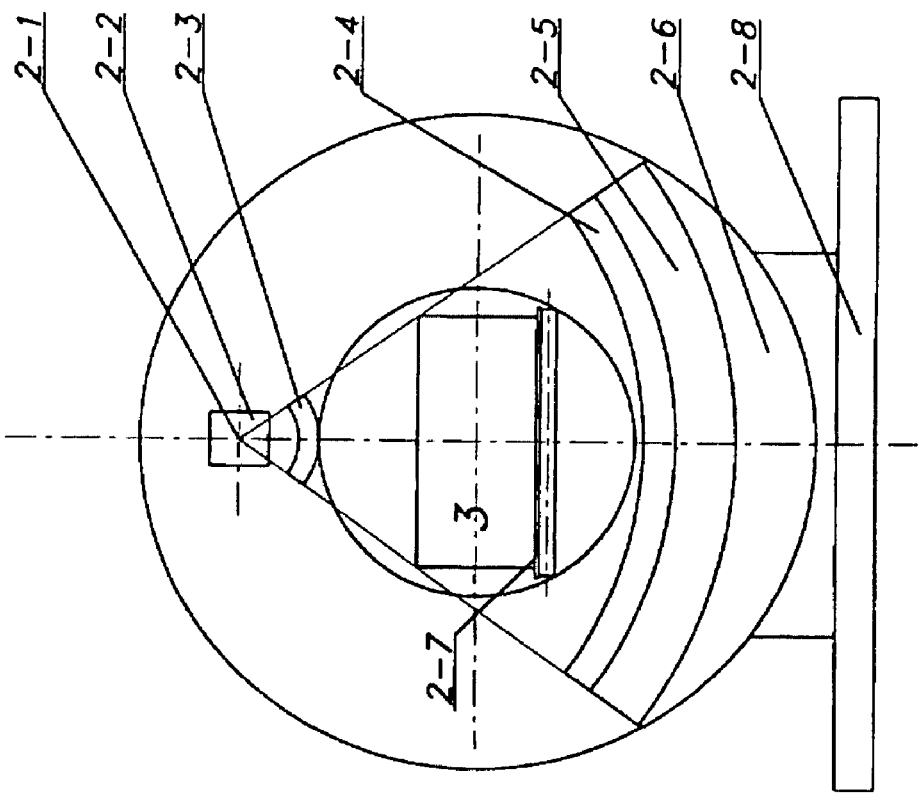
FIG. 4 is a front view of a CT subsystem of the radiation imaging system for nondestructive inspection of cases or luggage.

Firstly, the configuration and operation mode of the γ radiation imaging system for nondestructive inspection of cases or luggage will be described. As shown in FIGS. 1, 2, 3 and 4, the γ radiation imaging system for nondestructive inspection of cases or luggage of the present invention also comprises a DR subsystem I and a CT subsystem 2 in tandem. The DR subsystem 1 obtains a projection picture by line scanning a object-under-inspection 3, and the CT subsystem 2 obtains a tomographic image of the relative parts of the object-under-inspection 3 by rotary scanning, and judges whether flammable, explodable, drug or other prohibited articles is contained in the object-under-inspection 3 through density analysis. The DR subsystem mainly comprises a stationary frame 1-6, a translational conveying mechanism 1-7, and a shielding chamber 1-2 with $^{192}$Ir or $^{75}$Se radiation source 1-1 enclosed inside, a front collimator 1-3, a rear collimator 1-4 and an array detector 1-5 fixed onto the frame; The CT subsystem mainly includes a rotary frame 2-6, a translational conveying mechanism 2-7 capable of conveying cases and bags continuously or "step-by-step", and a shielding chamber 2-2 with $^{192}$Ir or $^{75}$Se radiation source 2-1 arranged inside, a front collimator 2-3, a rear collimator 2-4 and an array detector 2-5 fixed on the frame. The front and rear collimators are made of metal such as lead, iron or the like, or alloy, for collimating rays into a sheet shape, while eliminating the influence of the scattered rays. The numeral 2-8 in the figures represents a base of the CT subsystem.

The operation mode of the inspection system in the present invention is the same as the DR-CT inspection system in the prior art. During the inspection process, the object-under-inspection 3 (cases or luggage) are first translated through the DR inspection subsystem. The rays form a sheet-shaped radiation zone via the front collimator 1-3. After carrying out a line scanning of the object-under-inspection 3, the emitted rays are collimated again via the rear collimator 1-4, then received by the array detector 1-5 and converted into a projection picture via a data processing system. An inspector can determine which regions in the projected picture need a further judgment (CT scanning) according to the contour and grayscale of the projected picture. During the CT scanning process for the object-under-inspection 3, the related regions of the object-under-inspection 3 are transited into the radiation source irradiation field of the rotary frame 2-6 by the conveying mechanism 2-7. Driven by the rotary frame 2-6, the radiation source 2-1, the front collimator 2-3, the rear collimator 2-4 and the array detector 2-5 perform high speed rotary scanning (the rotary speed up to 360°/s, even to 720°/s) around the object-under-inspection 3, thus the array detector 2-5 transforms the detected rays, and then rebuilds and forms the tomographic image of the detected region through the data processing system, so that the inspector can judge the property of the article within the region from the material density represented by the image grayscale, thereby determining whether the region represents a prohibited article.

The present invention uses radioactive isotope ($^{192}$Ir or $^{75}$Se) instead of X-ray machine, wherein the radioactive isotope ($^{192}$Ir or $^{75}$Se) can emit γ rays with different energy. The mean energy of the γ rays is about 300 keV, which is apparently higher than the radiation energy of X-ray machine. The $^{192}$Ir or $^{75}$Se isotope γ rays have stronger penetration ability, and a high quality image can be achieved when being used for radiation scanning. Although compared with the X ray machine, the radiation level of the radioactive isotope ($^{192}$Ir or $^{75}$Se) source is lower by the scale of several times to several dozens times. But considering the functional requirement of the DR subsystem and the CT subsystem, the present invention provides a rational design for the relative components so as to absolutely avoid the adverse effect due to the low γ ray radiation level.

With regard to the whole inspection system, the functions of DR subsystem and CT subsystem are different, and their requirements for the radioactive source are also different. The DR subsystem seeks for a projected picture with a high spatial resolution, since the line scanning velocity required for securing a certain pass-through rate is not high, the desired radiation level is not high even if a small size detector is used. However, with regard to the CT subsystem, since high rotary scan speed is required to secure the pass-through rate, a higher radiation level is required if a small size detector pixel is used. But, according to the present invention, the function of the CT subsystem is to determine the material characteristics of the detected region, and then it should be mainly provided with a good density resolution. In view that even for dangerous articles, they will not be dangerous unless a certain total amount (a certain volume) is satisfied, so the CT subsystem does not have to provide a very high space resolution. For example, the petrol in 1 cm$^3$ weighs 0.7 g, so no danger exists. Therefore, the CT subsystem in the present invention can use a detector with a larger pixel size (e.g. 5×5~10×10 mm$^2$) so that the requirement for the radiation level is greatly reduced.

Another solution with regard to the low radiation level of the radiation source of $^{192}$Ir or $^{75}$Se radioactive isotope is to increase the expanding angle of irradiation field and to shorten the distance between the radiation source and the detector. Different from the bremmstraulung radiation emitting from the X ray machine, the -y rays from the $^{192}$Ir or $^{75}$Se radioactive isotope radiation source are substantially isotropic, thus an expanding angle of irradiation field larger than the previous can be selected. For example, the expanding angle for X ray machine is generally only 42°, while the expanding angle of the inspecting system according to present invention can be up to 70°-90°. In view of the radiation intensity is inversely proportional to the square of the distance, the shortening of the distance between the radiation source and the detector will obviously improve the radiation level at the detector.

According to different functional requirements of the DR subsystem and the CT subsystem, two luggage inspection systems are developed. In the first system, both the DR subsystem and the CT subsystem use the γ rays of radioactive isotope ($^{192}$Ir or $^{75}$Se) as radiation sources; in the second system, the DR subsystem still uses X-ray source, while the CT subsystem adopts the γ rays of radioactive isotope ($^{192}$Ir or $^{75}$Se) as the radiation source.

The two types of luggage inspection systems according to the present invention are described as follow.

I. Both the DR Subsystem and the CT Subsystem use γ Rays of Radioactive Isotope ($^{192}$Ir or $^{75}$Se) as Radiation Sources.

The radiation level of the radioactive isotope ($^{192}$Ir or $^{75}$Se) source is relatively low, which primarily affects the quality of the tomographic image obtained and rebuilt through a quick rotary scanning in the CT subsystem; however, this drawback can be overcome by enlarging the expanding angle of irradiation field so as to shorten the distance between the radiation source and the detector and then to improve the radiation level at the detector and enlarging the pixel size of the detector.

In the CT subsystem, γ-ray radioactive isotope source ($^{192}$Ir or $^{75}$Se) is enclosed in the shielding chamber 2-2, which is fixed on the rotary type frame 2-6 and rotates around the object-under-inspection 3 along with the rotary type frame 2-6 during the inspection process. The $^{192}$Ir or $^{75}$Se radiation source does not need power supply, furthermore the total weight of the radiation source plus the shielding container is relatively light, and so it is very suitable for a rotary scanning. The shielding chamber is made of heavy metal, such as tungsten or lead, and has a sufficient thickness, so that among the γ rays emitted from the radiation source, except for the available radiation emitted via the emitting port B, other rays in other directions are all shielded below a limitation value regulated by the radiation safety standards, which meets the radiation safety requirements. The active zone of $^{192}$Ir or $^{75}$Se inspection source (radiation source) is in the scale of millimeter level and sealed within a package made of double layer stainless steel, so the inspection system is very safe and reliable. Besides shielding rays, the shielding container helps to fix $^{192}$Ir or $^{75}$Se source firmly. As shown in FIGS. 5a, 5b and 5c, a cylindrical rotating shielding valve an arranged on the shielding chamber opens and closes the radiation source under the control of the control system. An emitting port B is disposed below the shielding container, so that the γ rays emitted from the port B is collimated into be a sheet shape by the front collimator 2-3 before penetrating the object-under-inspection, and then is collimated again by the rear collimator 2-4, and thus emits onto the γ ray array detector 2-5. The exit angle of the shielding valve A of the shielding chamber 2-2 defines the size of the expanding angle of irradiation field θ. In order to compensate for the low radiation level, the present invention fully takes advantage of the substantial isotropic characteristic for the radiation distribution of $^{192}$Ir or $^{75}$Se radioactive isotope source, and selects a large expanding angle of irradiation field (40°-90°). Thereby the object-under-inspection 3 can be fully covered, and the distance between the radiation source and the detector can be shortened, so that the radiation level at the detector can be improved. The array detector 2-6 arranged below the stationary frame could be any array detector suitable for receiving γ rays, preferably an array detector with a high detection efficiency and a high sensitivity such as a gas-pressurized array ion-chamber, a scintillation detector (e.g. a common cesium iodide or cadmium tungstate scintillation detector), a semiconductor detector, a multi-wire proportional chamber or a Geiger tube array detector. The arc length of the front and rear collimator and the array detector correspond to the expanding angle of irradiation field of γ rays.

In order to further lower the requirement for the radiation level, the present invention may adopt a detector with larger pixel size, e.g. 5×5–10×10 mm$^2$. in the case of the large pixel, the gas-pressurized array ion-chamber can better adapt to the requirement of providing a higher detection efficiency and sensitivity while maintaining an extremely low dark current (level of noise). Therefore such an ionization chamber is the most preferable.

The DR subsystem also adopts radioactive isotope ($^{192}$Ir or $^{75}$Se) as the radiation source, in which the shielding chamber and the expanding angle of irradiation field is the same as that in CT subsystem. The difference between the DR subsystem and CT subsystem lies in that the shielding chamber 1-1 is mounted on the stationary frame. Since DR subsystem is used to obtain a clear projection picture of a detected object, a high spatial resolution is necessary (by a detector with a small pixel size). At the same time, considering its operation mode is line scanning and the required radiation level is not high, it is feasible to use $^{192}$Ir or $^{75}$Se radioactive isotope radiation source. The array detector adopted by the DR subsystem has a small pixel size (e.g. 2×2 or 3×3 mm$^2$), preferably a scintillator-photodiode array detector or a gas-pressurized array ion-chamber is used.

II. The DR subsystem Adopting an X-ray Machine, while the CT Subsystem using γ Ray Radioactive Isotope ($^{192}$Ir or $^{75}$Se) as a Radiation Source.

Considering that DR subsystem scans and detects cases or luggage arranged horizontally (i.e. flatwise) in a vertical direction, the distance of penetrating the object is short, the requirement for the penetration ability is not very high, so even an X ray machine with 100~200 kV can also meet the requirement. Moreover, since the DR subsystem doesn't require a very high radiation level, it doesn't need a very high tube current when using an X ray machine as the radiation source. Thus a longer lifetime can be expected.

The CT subsystem in this case is the same as that in the first case.

The half-life time of $^{192}$Ir and $^{75}$Se is 74 days and 120.4 days respectively, and the operational lifetime for a general industrial $^{192}$Ir and $^{75}$Se inspection source is about 120 and 200 days respectively. During the lifetime, the radiation source can work continuously 24 hours per day. As a result, an inspection system using $^{192}$Ir or $^{75}$Se radiation source is very appropriate for the airport where a very high pass-through rate is required.

The following is a specific embodiment according to the present invention.

The DR subsystem 1, adopting a γ radiation source, comprises $^{192}$Ir or $^{75}$Se inspection source (radiation source) 1-1, a shielding chamber 1-2, a front collimator 1-3, a rear collimator 1-4 and an array detector 1-5 mounted on a stationary frame 1-6, and a conveying mechanism 1-7. The activity for the $^{192}$Ir or $^{75}$Se inspection source 1-1 is 1.95 TBq (50 curie). The shielding chamber (with a shielding valve) 1-2 is mainly made of tungsten, and the front and rear collimators are made of steel. The array detector 1-5 is a gas-pressurized array ion-chamber with a fine spatial resolution, whose pixel size is 3×3 mm$^2$. the detection efficiency of the array detector 1-5 is more than 40% for γ rays of $^{192}$Ir or $^{75}$Se. The distance between the entrance window of the ionization chamber and the radiation source is 0.95 m, and the flare angle of irradiation field is 72°. The conveying mechanism 1-7 is a conveying belt which conveys the cases with an adjustable velocity up to 12 m/min (equivalent to 720 cases per hour).

The CT subsystem 2 adopting a γ radiation source, comprises a $^{192}$Ir or $^{75}$Se inspection source (radiation source) 2-1, a shielding chamber 2-2, a front collimator 2-3, a rear collimator 2-4 and an array detector 2-5 mounted on a rotary type frame 2-6, and, a base 2-8 and a conveying mechanism 2-7. The activity of the $^{192}$Ir or $^{75}$Se inspection source 2-1 is 3.7 TBq (100 curie). The shielding chamber (with a shielding valve) 2-2 is mainly made of tungsten, and the front and rear collimators are made of steel. The array detector 2-5 is a gas-pressurized array ion-chamber, whose pixel size is 10×10 mm$^2$. the detection efficiency of the detector is more than 40% for γ rays of $^{192}$Ir or $^{75}$Se. The distance between the entrance window of the ionization chamber and the radiation source is 1.1 m, and the flare angle of irradiation field is also 72°. The rotary speed of the round frame is adjustable, the maximum of which is 720°/s. The conveying mechanism is of a roller type, both the transmission speed and the operation mode of which can be adjusted and controlled. The conveying mechanisms of both subsystems are joined in tandem with each other, while each of which works independently. The whole set of inspection device is provided with a same housing which can also be used to prevent form rays.

The invention claimed is:

1. A γ radiation imaging system for nondestructive inspection of a luggage, comprises a DR subsystem for obtaining a projection picture of the luggage by line scanning, and a CT subsystem for obtaining a tomographic image of the luggage by rotary scanning, wherein The DR subsystem including:
a stationary frame,
a conveying mechanism, and
a radiation source, a front collimator and a rear collimator, and an array detector,
which are fixed onto the stationary frame, the CT subsystem including:
a rotary frame,
a conveying mechanism, and,
a radiation source, a front collimator and a rear collimator, and an array detector,
which are fixed onto the rotary frame, characterized in that, the radiation source of the CT subsystem is a γ-ray source of $^{192}$Ir or $^{75}$Se radioactive isotope with a high specific activity, the γ-ray source is enclosed in a shielding chamber with a projecting shutter, the shielding chamber being fixed onto the rotary frame, the array detector is suitable for detecting γ rays of $^{192}$Ir or $^{75}$Se radioactive isotope, The radiation source of DR subsystem is a γ-ray source of $^{192}$Ir or $^{75}$Se radioactive isotope with a high specific activity, the γ-ray source is enclosed in a shielding chamber with a projecting shutter, the shielding chamber being fixed onto the stationary frame, the array detector is suitable for detecting γ rays of $^{192}$Ir or $^{75}$Se radioactive isotope.

2. A γ radiation imaging system as claim 1, wherein, the activity of $^{192}$Ir or $^{75}$Se radioactive isotope γ-ray source in both the CT subsystem and the DR subsystem is lower than 11TBq.

3. A γ radiation imaging system as claim 1, wherein, the array detector in the CT subsystem is one of a gas-pressurized array ion-chamber, a multi-wire proportional chamber, a Geiger tube array and a scintillation detector or a semiconductor array detector.

4. A γ radiation imaging system as claim 1, wherein, the array detector in the DR subsystem is one of a scintillator-photodiode array detector or a gas-pressurized array ion-chamber.

5. A γ radiation imaging system as claim 1, wherein, the expanding angle of irradiation field of the shielding chambers for the γ-ray source in both the CT subsystem and the DR subsystem is greater than 40°.

6. A γ radiation imaging system for nondestructive inspection of a luggage, comprises a DR subsystem for obtaining a projected picture of the luggage by line scanning, and a CT subsystem for obtaining a tomographic image of the luggage by rotary scanning, the DR subsystem including:
a stationary frame,
a conveying mechanism, and,
a radiation source, a front collimator and a rear collimator, and an array detector, which are fixed onto the stationary frame, the CT subsystem including:
a rotary frame,
a conveying mechanism, and, a radiation source, a front collimator and a rear collimator, and an array detector, which are fixed onto the rotary frame, characterized in that, the radiation source of the CT subsystem is a γ-ray source of $^{192}$Ir or $^{75}$Se radioactive isotope with a high specific activity, the γ-ray source is enclosed in a shielding chamber with a projecting shutter, the shielding chamber being fixed onto the rotary frame, the array detector is suitable for detecting γ rays of $^{192}$Ir or $^{75}$Se radioactive isotope, The radiation source of the DR subsystem is X-ray machine.

7. A γ radiation imaging system as claim 6, wherein, the activity of $^{192}$Ir or $^{75}$Se radioactive isotope γ-ray source in the CT subsystem is lower than 11TBq.

8. A γ radiation imaging system as claim 6, wherein, the array detector in the CT subsystem is one of a gas-pressurized array ion-chamber, a multi-wire proportional chamber, a Geiger tube array and a scintillation detector or a semiconductor array detector.

9. A γ radiation imaging system as claim 6, wherein, the expanding angle of irradiation field of the shielding chamber for the γ-ray source in the CT subsystem is greater than 40°.

* * * * *